United States Patent [19]

Thorner

[11] Patent Number: 4,644,945
[45] Date of Patent: Feb. 24, 1987

[54] PROTECTOR GARMENT FOR MEN

[76] Inventor: Robert H. Thorner, 32237 Willoughby, Farmington Hills, Mich. 48018

[21] Appl. No.: 481,888

[22] Filed: Apr. 4, 1983

[51] Int. Cl.⁴ .................................................. A61F 5/40
[52] U.S. Cl. .................................... 128/159; 2/403
[58] Field of Search .................. 128/157–162; 2/403–405

[56] References Cited

U.S. PATENT DOCUMENTS

| | | | |
|---|---|---|---|
| 4,014,044 | 3/1977 | Figueroa et al. | 128/159 X |
| 4,195,630 | 4/1980 | Connery | 128/159 |
| 4,345,337 | 8/1982 | Chung | 2/405 |

*Primary Examiner*—John D. Yasko

[57] ABSTRACT

The primary inventive concept herein relates to loose-fitting mens' garments which are in direct contact with at least the trunk area of the wearer, such as pajamas and woven "boxer" shorts (underwear), to provide protection for the wearer and his outer clothing from undesirable slight drainage of body-liquids (urine and semen) after normal termination of flow of these liquids, such as after urination. This drainage problem is experienced occasionally by entirely healthy men when they are careless or hurried after terminating the normal flow of these body-liquids. The new garment is also useful for men who are just starting to have a bladder-control problem, such as a slight delay in the normal closing of the sphincter muscle(valve), and even a minute leakage of the "valve" itself, which sometimes occurs in men as young as 30–35 years of age.

According to a primary concept of the present invention, a loose-fitting protector-garment for men is provided, and includes a penis-pouch or pocket having a unique shape, size, location and position in these garments to receive and contain the penis in an easy manner for the wearer, all to provide protection for the wearer and his clothing from a small but undesirable liquid-drainage from the penis after termination of body-liquid flow therefrom. This protection is further enhanced by liquid-proof means near the pouch to prevent these body-liquids from reaching the outer surface of the garment. According to several sub-combination inventive concepts, unique means are disclosed to render the penis-pouch to be readily accessible to the wearer of the loose-fitting garment. One sub-combination concept relates to means for providing vertical-rigidity in the free-wall of the pouch to prevent collapse thereof when the garment-wearer inserts his hand with the penis into the pouch; another sub-combination concept relates to unique means for causing the pouch to open automatically when the wearer's hand is inserted therein.

46 Claims, 9 Drawing Figures

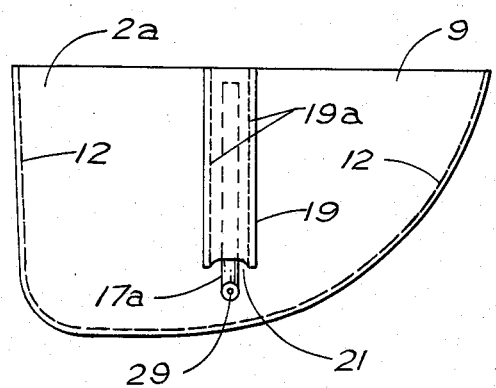
Fig. 4
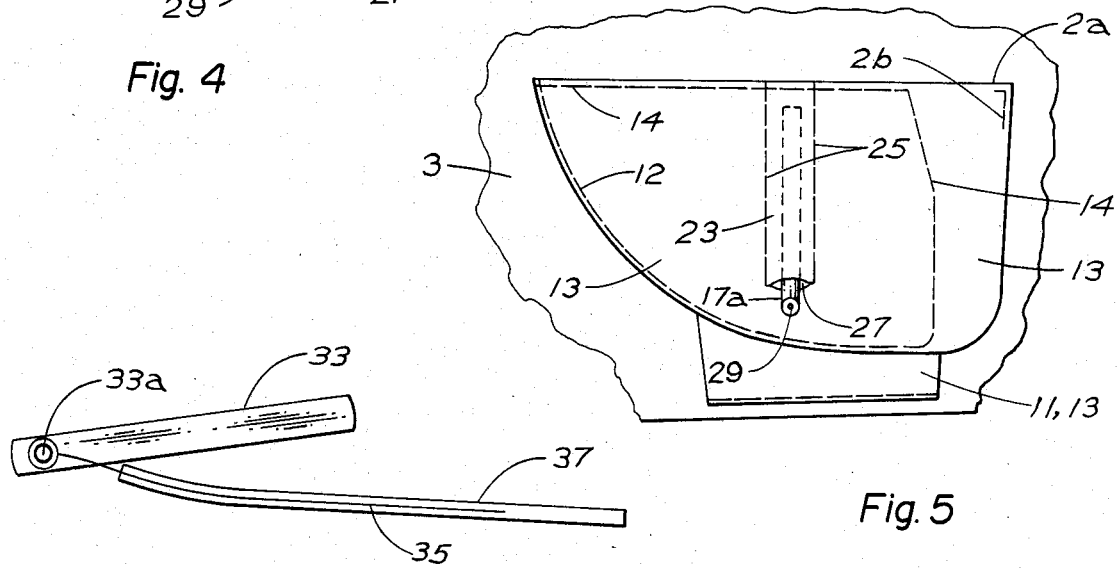
Fig. 5
Fig. 6
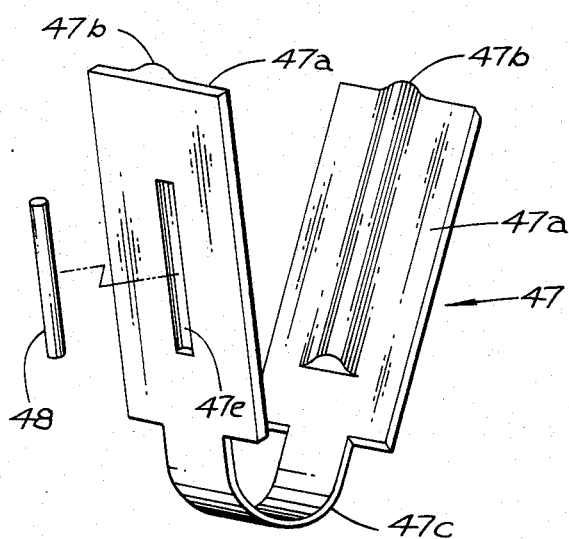
Fig. 8
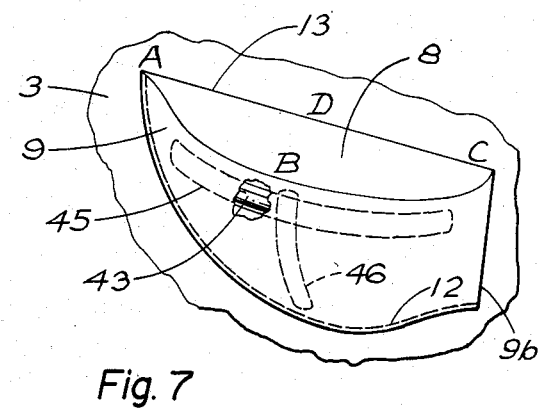
Fig. 7

PROTECTOR GARMENT FOR MEN

BACKGROUND OF THE INVENTION

The present invention relates to men's garments which are in direct contact with at least the trunk area of the wearer, but are characterized by being generally loose-fitting (such as underwear "boxer" shorts and pajamas) as opposed to men's garments which are generally snug-fitting (such as knit underwear shorts or briefs).

In order to understand the great utility of the present invention, it is first necessary to consider a thorough discussion of the problems of present and past undergarments for men and why they fail to provide the solutions to the problems set forth herein. The present invention relates to a normal problem inherent in the anatomy of all healthy men, and the invention also provides utility for those men who encounter a greater degree of this same problem.

It will be helpful to first consider a simple mechanical-hydraulic circuit comprising a reservoir, a pump or bellows (accumulator acting as a pump), a valve to control the liquid-flow from the pump, and a discharge nozzle. Examples might be an automotive carburetor, a portable garden lawn-sprayer, underground lawn plumbing, and many other hydraulic applications. In the similar human "hydraulic system" for controlling urinal storage and flow, the bladder comprises the reservoir as well as the "pump" (accumulator action); and the sphincter muscle comprises the "valve" for the flow of liquid (urine), and the penis is equivalent to the nozzle of the foregoing typical hydraulic system.

There is an important distinction, now to be explained, between the mechanical-hydraulic system and the human "hydraulic system", which distinction sets forth a problem which is solved by the present invention. In the mechanical hydraulic system, assume that the tip of the discharge nozzle is remote from the valve; then after the liquid-flow terminates when the valve shuts, a residual column of liquid exists in the hydraulic circuit between the valve and the nozzle-tip with no force to cause flow since the valve is closed. If the liquid column were vertical, it would act like a straw inserted in a glass of water; when a finger is held over the end of the straw while the straw is raised, a column of "trapped" water is raised with the straw because of the vacuum effect. In a typical mechanical-hydraulic circuit, it is helpful to note that the reservoir is made of solid material and the tubes are solid, the valve is solid, and the nozzle is usually made of metal or plastic which is also solid. In the human (male) "hydraulic-circuit", after termination of the flow of liquid (urine or semen), a column of liquid exists between the valve (sphincter muscle) and the nozzle tip (penis), and this column may be termed a "residual-liquid column".

The human "hydraulic-system" is exactly like the mechanical hydraulic system in all respects except that the human "nozzle" (penis) is fairly flexible and somewhat variable in length which can cause a problem worse than in mechanical hydraulic systems. Since the sphincter muscle is near the prostate, the "residual-liquid column" is about 4–6 inches long. Thus, the distinction is that the flexible components in the human hydraulic system make it more likely that a small portion of the residual-liquid column can be "lost" as a slight discharge or drainage because of flexing of the penis. Hence, with this anatomical mechanism (even with the sphincter "valve" closed), there can be an occasional slight discharge or dribble of urine from this residual-liquid column after flow-termination for all healthy men if they do not take enough time to handle this problem after urination. This same problem can apply for the same reason to the discharge or drainage of semen after sex activity as well as after urination.

This liquid-drainage may be very slight, such as only a few drops, and it may occur only when insufficient time is taken by the garment-wearer to prevent this slight residual-liquid drainage after terminating the liquid-flow, such as after urination. However, if the wearer of loose-fitting trunk garments is careless after urination, for example, a small residual-liquid drainage may cause embarrassment and discomfort, particularly for men wearing garments such as boxer shorts or pajamas, because these garments provide a generally loose fit on the wearer and do not absorb the slight liquid-drainage. Hence, woven boxer shorts and pajamas are examples of important garments intended for the present invention because the wearer of these garments have a problem occasionally with small residual-liquid drainage. Boxer shorts (and other "loose-fit" garments) will be considered herein to require a large amount of material compared to "snut-fit" (knit) briefs; and this "large amount" is sufficient to provide a substantially predetermined space between the wearer's leg and the leg-portion (and crotch-portion) of the garment to produce the "loose-fit" inherent in all boxer shorts.

If the wearer of boxer shorts spends enough time to prevent a small residual-liquid drainage after liquid-termination, there is no problem. But on some occasions, such as when men are late for an event or are just careless or absent-minded, they do not spend enough time and a small residual-liquid discharge can reach the outer surface of the shorts (or pajamas); this liquid-discharge can also reach the outer surface of the wearer's outer pants by capillary action, or by the liquid's directly contacting the outer pants at a point thereof below the shorts. In pajamas, the small liquid-discharge can also reach the outer surface in the same manner. This result in both garments can cause embarrassment and/or discomfort for the wearer.

Even if this small discharge actually occurs only on rare occasions, it can cause psychological concern just because of the knowledge that a liquid-discharge might occur (even if it does not), especially prior to business meetings or social gatherings. If the garment-wearer is hasty in returning the penis to his boxer shorts after urination or sex activity, and then sits in an automobile or chair wherein the outer pants are tight against the crotch area of the shorts, a few drops of liquid-discharge might reach the outer pants by capillary action to cause embarrassment, or even a stain. This is due to a slight loss from the "residual-liquid column" after the sphincter "valve" closes.

In addition to the "residual-liquid column" problem, even in healthy men, another problem can be caused by a slight time-delay before the sphincter "valve" closes; so it is necessary for the garment-wearer to take enough time after urination to accommodate both problems. It is also pertinent that some men, although entirely normal, have a slightly longer sphincter delay period than others. And of course, as men age, this delay-period can increase, and a real bladder-control problem can begin; then, even more time is required after flow-termination to prevent undesirable liquid-discharge.

One present "solution" to these occasional problems is to use another type of garment called "knit" shorts or briefs which are usually made wholly or partially of cotton and are fairly absorbent. Because these garments are snug-fitting and hold the genitals in the crotch-portion clear of the outer pants, a slight liquid-discharge from the penis will not cause any discomfort or embarrassment for the wearer.

The terminology used herein in relation to underwear shorts must be clarified. In the garment industry, the terms "woven" or "boxer" shorts are almost always used to describe the loose-fitting shorts, and these garments are usually made of polyester or part polyester and part cotton. The term "knit" shorts almost always refers to snug-fitting "athletic" shorts or "brief", and are usually made of 100% cotton or part cotton.

It should be noted that loose-fitting "knit-boxer" shorts are now being sold on the market. These garments have extended leg-portions like "woven" shorts, but have loose-fitting crotch and body portions and are otherwise similar to woven boxer shorts, except they are made of knit material, like 100% cotton. Therefore, these knit boxer shorts can be used with the present invention in the same manner as for woven boxer shorts. Thus, the material, per se, has no bearing no the application of the inventive concepts disclosed herein. However, in order to be consistent with terminology generally used in the garment industry, the term "woven" or "boxer" shorts will be used to denote base-fitting men's underwear, and the term "knit" shorts will refer to snug-fitting men's underwear. For boxer shorts, the leg-portions 3 and 5 which extend from the main body of the garment, have enough material to provide a substantially predetermined space between the wearer and these leg-portions to produce a generally "loose-fit" on the wearer.

Also, the term "liquid-termination" means that even with a slight delay of sphincter closure, or even with a small temporary leakage, the wearer considers the flow "terminated"; hence, "termination" is used herein in this context.

Most of the time in normal use of conventional boxer-shorts, no liquid-drainage problem is effected after liquid-termination if the wearer takes enough time after urination. But with these conventional boxer shorts, just to avoid the chance that liquid-discharge might happen, or on those occasions when a slight drainage will actually occur, the garment-wearer must either take sufficient time after liquid-termination if using boxer shorts, or he must change to knit shorts in which an occasional slight drainage causes no adverse effect because of their inherent snug-fit and absorbency.

The sale of knit shorts is about 8-9 times the sale of boxer shorts. One executive of a large manufacturer of these garments gave as the reason for this large sale of knit shorts that for babies, diapers are used, and knit shorts inherently provide a similar effect for young boys and adult males. A major premise for the present invention is that a large number of men consciously, or more likely sub-consciously, use knit shorts as a sort of "mini-diaper"; and they may not even be aware of this effect, even if their reason is only for security—just to be sure there is never a problem. As discussed above, knit shorts do indeed act as "mini-diapers" when this small problem occurs, which fact appears to be a main reason for in their large sale.

So far, the discussion has described only an occasional problem for completely healthy men for both body liquids, urine and semen. For the rest of the background discussion, it will help to consider special problems associated with only the bladder for a surprisingly large number of men (and women) as they progress through life. Many products are now sold for various degrees of bladder-control problems. These bladder problems usually develop gradually, but the degree of these control problems will now be classified in four groups, as follows:

CLASS-I comprises men who are entirely healthy, but who are careless after liquid-termination (of urine or semen) wherein a slight dribble can occur. In this class, the sphincter muscle closes completely in a normal time-period, although there might be slight variations in this period among men who are entirely healthy. These men have a problem only with garments like boxer shorts and pajamas, which problem is solved by the present invention.

CLASS-II comprises the many men who are just beginning to have a slight bladder-control problem because the sphincter muscle becomes slightly weaker, according to medical authorities, and hence is slower to close completely (but does close). Also, according to medical opinion, this early condition can worsen with age, but often is first noticed by men as young as 30-35. When these men wear free-fitting garments like boxer shorts, they must take more time than normal after liquid-termination to prevent embarrassment. But for most men in Class II, if they wear knit shorts there is no problem because of the "mini-diaper" effect of knit shorts, as discussed above. For this group of men, and also for men starting in Class III, a special absorbent liner can be made in accordance with the present invention for use in boxer shorts and pajamas, as will be discussed.

CLASS-III comprises the many men who develop a more severe bladder-control problem in which the sphincter muscle not only becomes slow to close, but also the muscle leaks slightly because it never quite closes. For this more advanced bladder-control problem, men (and women) usually must wear a special disposable absorbent liner in their undergarments which serves to a higher degree as an adult diaper than knit shorts alone without a liner. These absorbent liners are now being sold in large quantities at stores and supermarkets everywhere, and can be seen frequently in national television advertising.

CLASS-IV comprises men with a high degree or a total loss of bladder-control, which can occur for several medical reasons. For this extreme condition, stores and medical supply houses offer flexible containers strapped to the upper leg with a tube connected to the penis; or as an alternative, a full adult diaper is sold, and includes a large disposable insert that must be installed and removed as required.

Therefore, according to these classes, when men in Class I and most of Class II wear knit shorts, they would have no problem without any kind of disposable liner. For men in Class III (and the last portion of Class II), an absorbent disposable pad with adhesive strips is now offered on the market solely for use in knit shorts. This pad extends the "protection" of knit shorts for men in all of Class III, and possibly in the first part of Class IV, by using slightly larger liners. For a more severe bladder-control problem for men entering Class IV, progressively larger absorbent diaper-type pads (liners) must be used. For total loss of bladder-control in Class IV, a diaper-type garment is used.

From this classification, there are clearly several considerations in relation to urinary problems. The first consideration is the "residual-liquid column" for entirely healthy men after the sphincter "valve" is closed, as explained above. The second consideration is the normal time required for the sphincter "valve" to close, which varies among healthy men. A third distinct consideration is the increase in this closure time as men advance in age. And a fourth distinct consideration is the beginning of a real bladder-control problem when the sphincter "valve" never quite closes. All of these considerations are accommodated by the loose-fitting garment of the present invention.

The present large sale of knit shorts in relation to boxer shorts, as mentioned above, helps to confirm the extent of the problem for reasonably healthy men. Based on discussions with many men, it appears that a large share of men who use knit shorts, whether consciously or sub-consciously, may do so to avoid the problems of occasional liquid-discharge after liquid-termination, such as after urination. Hence, it would appear that the "mini-diaper" effect is indeed a principal reason for the large sale of knit shorts, because in fact they are so objectionable for many reasons.

There are many objections to knit shorts as follows: (1) knit shorts are very uncomfortable because of their confinement and restriction of the genitals; (2) knit shorts reduce air-circulation; (3) knit shorts are somewhat difficult to use for urination compared to boxer shorts; (4) knit shorts when hand-washed, dry slower than woven shorts, especially if the woven shorts include polyester; this is useful for travelers who wash their shorts in motels to dry overnight; (5) knit shorts are less flattering in appearance for stout and obese men than are boxer shorts; (6) according to recent reports, knit shorts because of their snug fit can reduce fertility (to be discussed); (7) knit shorts are less hygienic (urine contacts skin); and (8) while the unit price of knit shorts is about 25% to 35% less than that of boxer shorts, if my own experience is typical, knit shorts must be replaced at least twice as often as boxer shorts; the crotch portion eventually stretches and curls, which gives a feeling that the genitals might "fall out". Also the nap eventually starts to fall out. If this is characteristic, then knit shorts are more costly to use—even with the added cost of the garment of the present invention. Despite these many objections, many men knit shorts just to preclude the chance of an occasional liquid-drainage problem.

Regarding the fertility factor, in a recent professional television piece entitled, "Creation of Life", the magnified live male sperm with the testicles at normal temperature were shown. When the temperature of the testicles was raised just a few degrees above normal, the magnified view showed clearly the increase in defective live sperm. Nature usually designs biological mechanisms for a reason. The testicles of male primates are designed to be outside the body and suspended free and unrestricted. It was pointed out in the program that although humans must wear clothing, loose-fitting clothing (such as underwear) is most desirable in this respect. Knit shorts, being more confining, inherently tend to raise the temperature of the testicles, which also increases the risk of testicular cancer according to recent medical reports; although this risk is not large (6000 men per year), the highest incidence of cancer in the age group of 20–34 is testicular cancer.

The prior art discloses structures for protector garments which appear to fall into two classes. In the first category, absorbent padding is sewn to the inside wall of men's garments to provide protection from body-liquid-discharge. The problem with this construction is that the discharged liquid can reach the lower leg of the garment-wearer when standing or walking; and for boxer shorts with this padding, the liquid-discharge can reach the inside lower portion of the outer pants. The second category of prior art discloses various penis-pouches; but the structures disclosed in this prior-art are either inoperative or at least difficult, and are uncomfortable and/or inaccessible to perform the useful functions of the present invention. While penis-pouches have been disclosed in the patent art, just any pouch will not solve the problems discussed above. A special pouch or pocket is necessary, which is the subject of the present invention.

There is no prior art known to me at present that discloses the inventive combinations and concepts set forth herein, which provide such useful solutions to all the problems discussed above; this result is accomplished by providing a loose-fitting garment like boxer shorts with a useful and practical penis-pouch acting as a "mini-diaper", but without all the many objections listed above for knit shorts. Although the prior art has offered no useful inventive concepts which solve these problems, as does the present invention, at least the prior art establishes that these problems do exist and have been recognized by those skilled in the art, and further that the concepts of the present invention have eluded those skilled in the art for many years.

A primary concept of the present invention relates to a mens' loose-fitting trunk garment having a penis-pouch to prevent the occasional "liquid-drainage" (as defined above) from reaching the outer surface of the garment, and in which the pouch is designed and positioned in a particular manner and with a special size and shape, to enable easy insertion into the pouch of the wearer's hand with the penis before and after urination or after sex activity. I have found that boxer shorts made according to this inventive combination are very useful because they are comfortable, they are easy to use for urination, they provide a mini-diaper effect as for knit shorts, they provide complete freedom from genital confinement without awareness of the existence of the pouch, they provide good air circulation, they are very easy to hand-wash with fast-drying, and presumably they can be sold at lower overall cost compared to knit shorts; also, according to reports, they do not decrease fertility.

Hence, a main overall purpose of the present invention is to provide in any loose-fitting men's garments, such as boxer shorts and pajamas the same "protection" from body-liquid-discharge which is inherent in knit shorts with their "mini-diaper" effect, but without all the objections of knit shorts.

Thus, a primary inventive combination of the present invention includes a pouch or pocket forming a chamber to receive the penis, in which the pouch has a particular shape, size, location and arrangement of components in relation to the crotch and leg-portion as well as to the penis opening (fly opening) of a loose-fitting garment such as boxer shorts and pajamas. This inventive combination is characterized by mounting the pouch in the vicinity of one of the leg-portions, and includes liquid-absorbent means (which may include liquid-proof means) to prevent any penis-discharge from reaching the outside surface of the garment, thereby avoiding any possible embarrassment and discomfort for the wearer. More specifically, this inventive combination further provides that the top-portion of the free-wall of the pouch be located somewhat near the bottom of the flap-opening of the garment to enable easy access for the wearer to deposit the penis in the pouch. This inventive combination also provide that the top portion of the pouch be generally horizontal to help provide this easy access to the pouch by the wearer. This inventive combination further includes the location of the pouch in a loose-fitting garment, such as boxer shorts which has a flap-opening for the penis, so that at least a major portions of the pouch is mounted on the leg-portion that includes the outer flap-portion forming the opening, again to enable easy access to the pouch. The inventive combination also includes provision that the pouch-chamber be a particular "large size", to be defined hereinafter.

A very useful sub-combination concept in this disclosure is to provide a penis-pouch in its broadest form, in which means are provided to maintain sufficient longitudinal (vertical) rigidity in the free-wall of the pouch to enhance the easy accessibility of the pouch for the wearer. In another particularly useful subcombination concept, a pouch means is disclosed in its broadest form, for loose-fitting garments like boxer shorts, in which means are provided to urge the free-wall of the pouch to move automatically in an opening direction. This pouch-opening-means may comprise force-producing means, such as spring means and/or weight-means acting on the free-wall, or just a particular shape and design of the free-wall itself in forming the open chamber of the pouch.

For men having a minor degree of an actual bladder-control problem, as in Class II and the start of Class III as discussed above, a special disposable absorbent liner which is made according to the present invention can be provided for the pouch. The main inventive concept may include other important aspects to be discussed.

OBJECTS OF THE INVENTION

A main object of the present invention is to provide a loose-fitting "protector" garment which is in direct contact with the wearer, and protects the wearer and/or his outer pants from any penis-discharge, such as urine or semen, and further to prevent this liquid-discharge from reaching the outer surface of the garment;

Another object of the present invention is to provide a protector-garment as set forth in the preceding object which does not confine the genitals in any way, and is so comfortable that the protector garment feels no different to the wearer from ordinary pajamas or boxer shorts while providing the benefits specified in the other objects recited herein;

An additional object of the present invention is to provide a protector garment as set forth in the preceding objects which facilitates easy use for urination;

A particularly important object of the present invention is to provide a protector garment as set forth in the prior objects, which includes a penis-pouch as the means providing the protection from liquid-discharge, and in which the garment makes it very easy for the wearer to deposit and remove the penis in the pouch;

Another object of the present invention is to provide a protector garment as described in the prior objects and which is less costly in continuous use for the wearer than present garments which inherently include such protection;

Another object of the present invention is to provide a protector garment as set forth in the prior objects, which does not diminish the normal fertility of men while providing the protection from liquid-discharge and ease of use, as described herein;

Other objects and advantages of the invention will become apparent from the following description, and from the accompanying drawings, in which.

Figure 1:
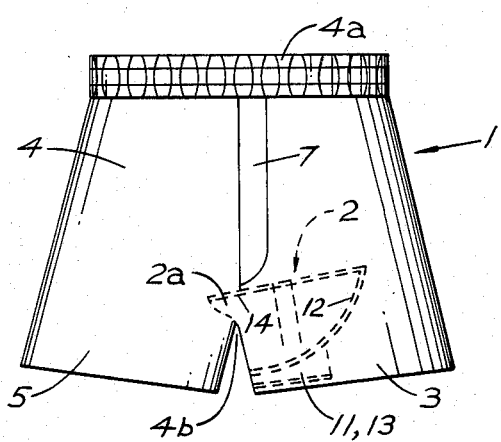
FIG. 1 is a front elevational view of one form of protector garment of the present invention, illustrated as boxer shorts as normally worn, with the penis-pouch properly shown in dotted lines.
Figure 2:
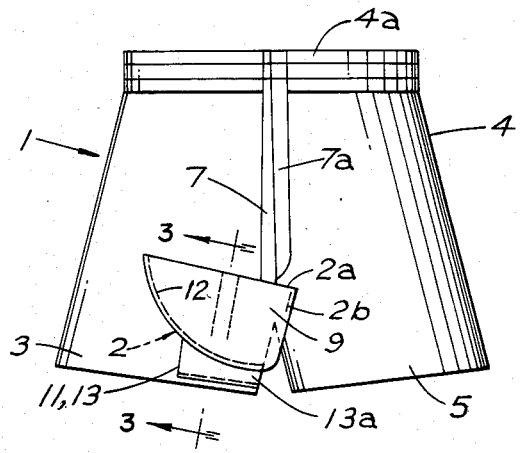
FIG. 2 is another view of the garment shown in FIG. 1, but with the illustrated boxer shorts turned inside out to show the penis-pouch as it would appear in this condition.
Figure 3:
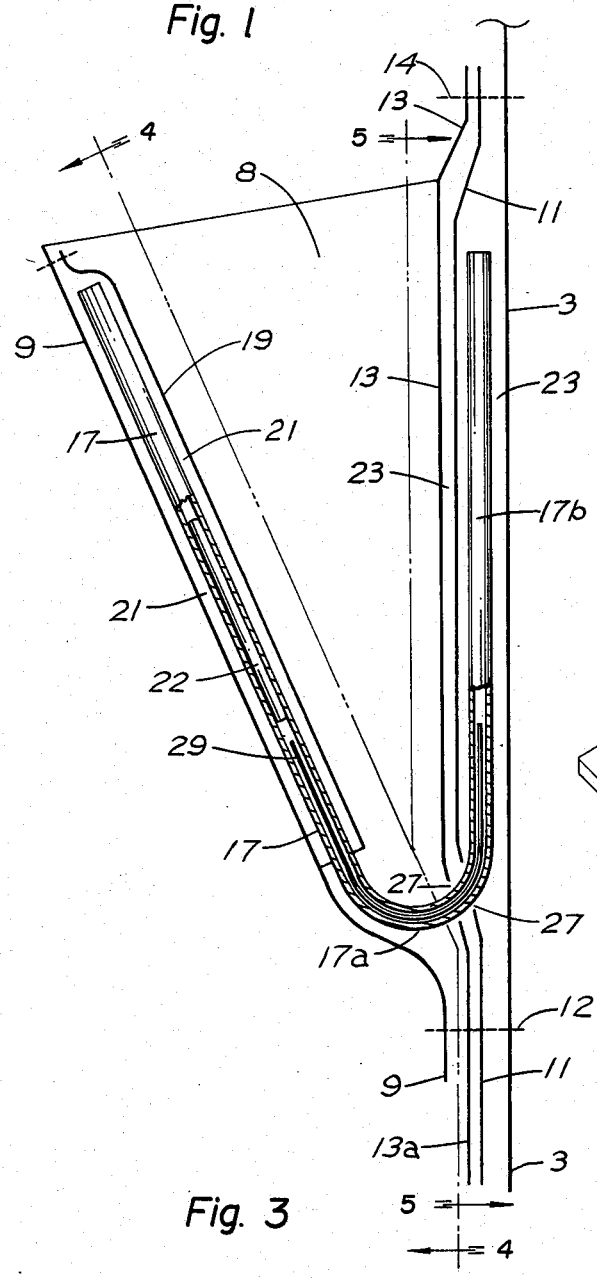
Figure 9:
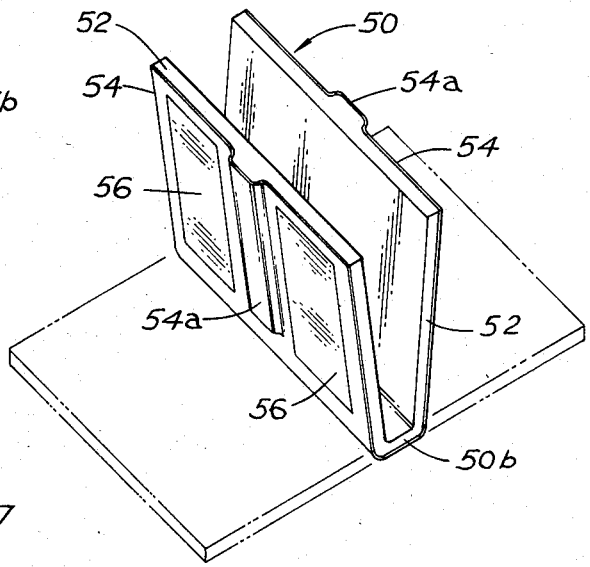

FIG. 3 is an enlarged exaggerated partial sectional view of the boxer shorts illustrated in FIG. 2, taken along line 3—3 in FIG. 2, and in which the sections are shown only as lines for clarity because the walls are so thin, and particularly illustrating a typical penis-pouch of the present invention and one form of force-producing means urging the pouch in an opening direction, and with the fabric pieces spaced for clarity, although the pieces are actually sewn together in a manner to be explained;

FIG. 4 is an elevational view of the free-wall forming the penis-pouch shown in FIGS. 1-3, taken along the line 4—4 in FIG. 3;

FIG. 5 is a fragmentary elevational view of the illustrated boxer shorts and particularly the inner wall of the penis-pouch shown in FIGS. 1-3 taken along the line 5—5 in FIG. 3;

FIG. 6 is a detail perspective view of one form of the spring means urging the free or movable wall away from the leg-portion of the boxer shorts or pajamas, and also illustrating another form of longitudinal (vertical) ridigity means;

FIG. 7 is a perspective view of another form of a penis-pouch of the present invention having an inherent construction tending to urge the flexible free-wall of the pouch to move in an opening direction:

FIG. 8 is a perspective view of another form of force-producing means to urge the free-wall of the pouch in an opening direction;

FIG. 9 shows a special disposable absorbent insert or liner made according to the present invention for men with slightly greater-than-normal dribble and particularly adapted to be inserted in the penis-pouch illustrated in FIGS. 1-5 and 7.

It is to be understood that the invention is not limited in its application to the details of construction and arrangement of parts illustrated in the accompanying drawings, since the invention is capable of other embodiments and of being practiced or carried out in various ways. Also, it is to be understood that the phraseology and terminology employed herein is for purposes of description and not of limitation.

Now consider in detail a discussion of the forms of the invention illustrated herein to show how loose-fitting garments like boxer shorts, when made according to the present invention, act as "mini-diapers" like knit shorts but without all their problems. FIG. 1, by way of illustration, shows a pair of boxer shorts 1 having a pouch or pocket means 2 properly mounted on the left leg-portion 3 of the shorts in relation to a body-portion 4, as worn, but with a small portion 2a of the pouch 2 residing on the right leg-portion 5. In FIG. 2, the shorts are shown turned inside out wherein pouch 2 can be seen clearly.

As shown in FIGS. 1 and 2, the pouch 2 is preferably mounted on the same leg-portion that includes the outer flap-portion; this would be the left leg-portion 3 which extends into the outer flap-portion 7 as illustrated in FIGS. 1 and 2. The inner flap-portion 7a is part of leg-portion 5 (FIG. 2). All boxer shorts and pajama pants, as well as regular (outer) pants, are designed for insertion of the right hand through the flap (fly) opening, so the outer flap-portion 7 is on the wearer's left side; therefore, most of the pouch 2 resides on the left side of center in "right-handed" shorts. While "left-handed" shorts, pajama pants and outer pants are not available, they could be made in which the forms shown in FIGS. 1 and 2 would be reversed. Also, for the purpose of this invention, it makes no different whether the flap-portions include buttons or zippers, or just remain open at all times, as in most boxer shorts. Also, for definition, it makes no difference whether the "aperture" or "opening" formed by the flap-portions (sometimes called "fly" opening) or another type of opening is vertical, curved or has other types of apertures, providing the pouch 2 is readily accessible.

A chamber 8 is formed by a free-wall 9 of the pouch which must be large enough to enable insertion therein of at least a portion of the hand with the penis; but this requirement caused further problems to be solved. With a large pouch, as described thus for, the free-wall 9 of the pouch sometimes tends to collapse and/or curl when the wearer inserts his right hand with the penis into the pouch, so the pouch is often somewhat difficult to enter. Therefore, the large size of the pouch can be a component of a primary inventive combination. The limits of the term "large size" can be established for definition. The pouch-chamber 8 must be "large" enough so that most men can insert at least a portion of their hand (with the penis) into the pouch chamber. Since a large number of men's fists will fall into a predetermined range of sizes, the proper "large size" is thereby established. The important fact in this consideration is that if the pouch, as described thus far, is "large enough" to receive a portion of a man's hand, the free-wall 9 sometimes tends to collapse and/or curl. Hence, the rigidity and opening of the free-wall of the pouch becomes significant in sub-combination inventions to be discussed. Therefore, when the term "large size" is used in the claims, it is to be interpreted in this context.

In the preferred form of pouch means, at least a major portion of the free-wall 9 is positioned (as by fastening means) adjacent to the leg-portion of the garment that includes the outer flap-portion 7. This result can occur in effect even if the free-wall is not connected directly to leg-portion 3, but is connected only to a separate piece, such as absorbent-piece 13 for example, which in turn is directly connected to the leg-portion; hence, in this form of pouch means the free-wall is "operatively connected" to the leg-portion.

Also, I found in tests that the movable free-wall 9 of a large pouch, as described thus far, sometimes tended to hug or cling to the leg-portion of the garment, such as after laundering. This was somewhat frustrating, since there is room for only one hand to be inserted through the opening formed by the flap-portions, so it was necessary to "open" the pouch manually while holding the penis when this problem occurred.

I provide several useful means to solve these puzzling problems. As shown in FIGS. 1 and 2, the pouch 2 is large enough to permit the wearer's hand with the penis to enter the pouch easily. Also, the top of the pouch 2, and particularly the free-wall 9 thereof, is located somewhat near the bottom of the fly-opening formed by the flap-portions 7 and 7a, as shown in FIGS. 1 and 2, in order to allow the penis to be easily deposited and reside in the pouch without restraint or discomfort. The main portion of the pouch 2 is positioned far enough in leg-portion 3 to provide ample room to render the penis free of any restraint for ease of entry into chamber 8 and for maximum comfort. For additional room, I also found it extremely useful, but not essential, to extend the inner end 2a of pouch 2 to the other leg-portion 5 and secured, as by "tacking" with separate threads 2b (FIGS. 2 and 5), or by extending the upper thread straight over into leg-portion 5 about 1-1½ inches on the other side of the center-seam of the crotch-portion of the shorts.

This useful combination includes positioning a minor portion of the pouch 2 adjacent to the leg-portion 5 past the center seam of the crotch-portion 4b as far as necessary, so that extension 2a enables the pouch to open enough to provide complete freedom of the penis in normal wear. The pouch is also positioned so that the top of the pouch, and particularly the free-wall 9, is "generally horizontal"; this term is intended to mean that the top of the pouch might be at a slight angle, such as 10°–18° as illustrated in FIGS. 1 and 2, wherein the pouch-top might be substantially parallel to the bottom of the leg-portion of the boxer shorts as shown.

Means are provided to render the outer surfaces of leg-portion 3 and at least a portion of pouch 2 free from body liquids (such as urine or semen), which is made clear in FIG. 3. This enlarged view is exaggerated for clarity, because it is difficult to show layers of thin cloth sewn together, each having only 0.006–0.13 thickness. Hence, the layers are shown separated and as lines without thickness, although they are sewn or cemented together in a manner indicated in the figures.

Liquid-absorbent means, which may include liquid-proof means, are provided in association with one leg-portion of the garment to maintain the outer surface thereof, at least in the area adjacent to the pouch, free of even a minute amount of liquid-discharge from the wearer. In the form illustrated in FIGS. 1–3, the liquid-absorbent means includes a liquid-proof piece 11 adjacent the inside of the left leg-portion 3. The piece 11 may be made of soft material such as vinyl, rubber, urethane or any other flexible liquid-proof material. In the form shown in FIGS. 1–5, the liquid-absorbent means also includes a separate woven cloth or other mildly-absorbent piece 13 which has the same shape as the liquid-proof piece 11 in the pouch and is adjacent thereto. Hence, for this form of liquid-absorbent means, the piece 11 has no absorbent material bonded thereto. In another form of liquid-absorbent means, a mildly absorbent material, such as cotton or woven cloth, is clad or bonded to the inside wall of the liquid-proof piece 11; in this form of the invention, the separate piece 13 is not used. Such bonded material is available in large rolls and the piece 11 is cut from the rolls. In a less costly modification of liquid-absorbent means, the piece 11 can be omitted if the leg-portion 3 is sprayed (such as by "Scotch-Gard") or otherwise treated on its outside surface to be liquid-proof, and the absorbent piece 13 is used alone; in this modification, any mildly absorbent woven cloth, such as cotton-polyester, may be used. In still another form of pouch means, the two pieces 9 and 11 may be replaced by only a single piece of absorbent means, such as cotton-clad urethane, and folded to form the entire pouch 2 (similar to the liner 50 in FIG. 9, to be discussed).

The movable wall 9 is secured to the leg-portion 3 (and pieces 11 and 13) by suitable fastening means, such as by adhesives, or by a thread seam 12 as illustrated, to position the pouch 2 in relation to this leg-portion. Also, the pieces 11 and 13 are otherwise secured to the leg-portion 3, as by thread-seam 14 (FIG. 5). For men in Class I and most of Class II, it is highly desirable, if not essential, to make the free-wall 9 waterproof; if liquid-proof material is not used, it is acceptable to spray the outside surface of wall 9 with a liquid-proof material similar to "Scotch-Gard" but permanent, which also renders the thread holes liquid-proof.

In the simplest and least costly form of liquid-absorbent means, both the liquid-proof piece 11 and absorbent piece 13 can be omitted so that the free-wall 9 is then secured directly to the leg-portion 3. Then the leg-portion is sprayed or otherwise treated on its outside surface with a liquid-proof material.

Tests have shown that liquid-discharge might pass occasionally through holes in the seams made by sewing needles. It may be useful to apply a liquid-proof sealant or other treatment to the seams after completing the garment, or the free-wall can be attached to the leg-portion 3 by an adhesive. The absorbent piece 13 has an extension 13a to absorb any liquid-droplets that might reach this area by capillary action, but these droplets would not reach the outer surface of the garment.

As explained above, the pouch must be large enough to permit entry of a portion of the wearer's hand with the penis without collapsing and/or curling the free-wall 9. If the entire free-wall were too rigid, it would not provide the necessary flexibility, because the wearer must feel no difference with or without a pouch. Several rigidity means are illustrated in FIGS. 1–8 to provide a proper *degree* of longitudinal (vertical) rigidity of the free-wall 9. In the forms illustrated in FIGS. 1–5, the rigidity means comprises a semi-flexible rubber or plastic strip-like member 17 held to the free-wall 9 by channel means such as a cloth strip 19 (FIG. 4) sewn to the free-wall by seams 19a to form a sheath or vertical channel 2 into which the strip-member 17 is inserted.

For vertical rigidity, I have used synthetic rubber (or plastic) chord, tubing or flat strips, etc. In FIG. 3, a more rigid piece 22 made of metal, plastic, etc., might be inserted inside tube 17 for a portion of free-wall 9 to help provide sufficient vertical rigidity of the free wall. However, tests have shown that the rubber strip-member 17 by itself (such as a silicone rubber tube or chord having 5/32" dia. and 70 durometer) appears to provide acceptable rigidity. If the free-wall were too rigid, it would be uncomfortable for the wearer. Although piece 22 can be of any length, if used, tests have also shown that a metal dowel about 1/16" to 3/32" diameter, for example, and about 1" to 2" long when inserted in part of the rubber tube 17 and/or in the free-wall 9 can supplement the rigidity, but is not essential. A silicone or natural rubber chord, for example, (of about 5/32" diameter and 70 durometer) gives sufficient vertical rigidity, without any cognizance by the wearer. No rigidity member appears to be necessary in the portion 17b, according to tests to date. The rigid-piece 22 can provide another important use, as will be discussed.

As explained above, in a sub-combination concept, means are provided to automatically urge the free-wall 9 in an opening direction to make it easy for depositing the penis into the pouch after same is open. The term "free-wall", as used herein, refers to the fact that the unsecured portion of wall 9 is flexible and movable to and from the leg-portion 3. The wall 9 normally resides close to the leg-portion, but the wall must temporarily move away from the leg-portion to form the open-chamber 8 for enabling the deposit of the penis therein. But wihout this opening-means, sometimes the free-wall clings to the leg-portion 3 to make it somewhat difficult to open the pouch.

In an important form of the means to urge the free-wall in an opening direction, force-producing means are provided to produce a very gentle force to open the free-wall. The force must be low enough in order to avoid a bulge of the outer pants in normal wear. In the form of force-producing means illustrated in FIGS. 3–5, the strip-member 17 at portion 17a provides a spring-action in addition to the vertical rigidity for the free-wall 9; tests have shown that the spring-rate of a (synthetic) rubber chord, tube or strip, for example, is sufficient to provide the necessary gentle spring-force for moving the thin light-weight cloth of free-wall 9 in an opening direction. Referring to FIG. 3, the spring-portion 17a of strip member 17, which in the example shown is made of the proper rubber composition (or certain plastics), inherently provides this gentle spring-action. The portion 17b of member 17 extends into a sheath or channel 23 formed by seams 25 in the absorbent-piece 13 which is suitably secured to the leg-portion 3, as by threads; the illustrated channel construction is shown best in FIG. 5, and is formed by the two seam lines 25. Also, a slot 27 is cut in pieces 11 and 13 (FIGS. 3 and 5) to provide an entrance to the vertical channel or sheath 23, now formed by the left leg-portion 3 and the liquid-proof piece 11, as illustrated in FIG. 3, or it could optionally be formed by the absorbent-piece 13 if the strip-extension 17b were inserted between pieces 11 and 13. In another form of sheath means, a separate cloth member similar to strip 19 may be secured only to absorbent piece 13 (or to 11 if 13 is omitted) to form the sheath.

Tests have shown that the tubular (or chord) rubber member 17,17a, and 17b (of proper composition and durometer) when inserted in the two channels or sheaths 21 and 23 has a natural bending spring-rate which is acceptable to provide the gentle spring-force necessary to open the thin cloth free-wall 9, as shown best in FIGS. 3,4 and 5. In this form of force-producing means, both the vertical rigidity for the free-wall 9 and the spring force can be provided by a single element (strip 17), although the rigidity means may be separate from the force-producing means, as will be illustrated. Another rigid element, like rigid-piece 22, can be inserted in the tube member portion 17b if desired, although tests to date indicate that rubber chord or tubing provides adequate rigidity.

In another form of force-producing means, a metal spring may be provided to supplement the rubber tube (or chord) 17a. In FIG. 3, the strip-member 17 is illustrated as a rubber tube providing some inherent spring-action in portion 17a. If a more consistent spring-action is desired to open the pouch, a steel wire spring element 29 (such as music wire) may be inserted inside the tubing portion 17a, although tests have shown that rubber chord is preferable for spring element 29 (such as 3/32" dia. silicone or natural rubber). With this construction, the total spring-rate comprises the spring-rate of the rubber tube plus the wire spring-rate in bending. The metal wire diameter is small (such as 0.010"–0.014) to provide only the necessary low force to open the pouch. A rubber (or plastic) flat strip-member also can provide an acceptable low spring force. Also, according to tests to date, some compounds of rubber or other rubber-like material (synthetic) with non-uniform cross-sectional shapes and without the metal spring can provide sufficient spring action. However, a strip-member made of metal spring material has a more consistent spring-rate, and can supplement or even replace the spring-portion 17a if desired.

The rigidity-means for the free-wall 9 is shown in FIG. 3 as part of the spring-means (rubber tube 17, 17a, 17b); but the strip-member 17, acting as a rigidity element, can be made of tubing or chord (such as 5/32" dia. silicon or natural rubber) with a length similar to the cloth strip 19 close to the bottom of the pouch, and the rubber spring-portion 17a can be separate (such as silicon chord with 3/32" dia.); or the metal spring 29 can be provided separately if used, as illustrated in FIG. 3. In another alternative the wire spring may be inserted as part of a molded rubber strip-member 17.

Another form of force-producing means is also illustrated in FIG. 3. The rigid-piece 22 which is shown inserted in part of strip-member 17 adjacent the free-wall 9 (FIG. 3), also comprises a force-producing means because of the weight effect, which must be small. Hence, the rigidity-piece 22 is also a "weight-piece". The weight-piece 22 may comprise a small metal dowel or rod inserted in channel 21, for example, so its weight urges the free-wall to move in an opening direction. The weight-piece 22 can be of any length, but is shown for only part of the length of the free-wall 9, because the rod must be small to keep the weight-force small. The weight-piece 22 may be used if desired with or without a spring-portion 17a and/or wire 29, but a rubber spring-portion helps to start movement of the free-wall 9. Hence the weight and spring-force can supplement each other. The natural weight of the rigidity-piece if made, for example, of about 0.160–0.190" dia. silicone or neoprene rubber chord appears to be sufficient to provide some weight action. If additional weight is needed, a small metal piece such as a brass strip about 5/16" to 3/8" wide and 0.015–0.020" thick can be wrapped around the upper end of the chord, for example.

It can now be understood that the present invention comprises a unique combination of elements and conditions relating to a loose-fitting men's garment, such as boxer shorts and pajamas, which together make the wearer entirely unaware than a penis-pouch exists in the garment while providing complete dribble-protection. The unique combination of elements and conditions which produces this desirable result comprises at least a pouch of sufficiently large size and positioned on the leg-portion of the garment that includes the outer flap-portion, such that the top-portion of the free-wall is substantially horizontal and located somewhat near the bottom of the flap-opening; the protector garment is greatly enhanced by extending the pouch past center into the other leg-portion, and is also greatly enhanced by the unique rigidity means and automatic pouch-opening means which is operatively connected to the free-wall.

In actual practice, in order to achieve this desirable result, the depth of the pouches made to date has been about 4", but has varied plus or minus ½"; the width of the pouch at the top has averaged about 5¾", but has been varied about plus or minus ½". The pouches to date have been positioned by fastening means such that the top-portion of the free-wall is usually somewhat near the bottom of the fly-opening, such as ½" above this point to about 1" below same; also the pouches of the protector garment have been extended past the mid-position of the garment an average of about 1⅞", but have varied from 7/8" to 1 7/16". The present protector garments include a waterproof "barrier" comprising a single piece of urethane fabric (about 0.010" thick) which is coated with an absorbent material on the pouch-side to combine elements 11 and 13 (FIG. 3); this material appears to be satisfactory, although several other materials have been used successfully.

FIG. 6 shows another form of spring means which can be used to open the pouch, although not a preferred form according to tests. In FIG. 6, a plastic or metal strip 33 is connected to a metal spring element, such as music wire 35 as illustrated. The wire includes a loop secured to one end of the strip 33, as by a rivet 33a secured through the wire loop and a washer. The strip 33 is inserted in channel 23 through slot 27 while the wire spring 35 alone is inserted into channel 21 to act on the free-wall 9 in an opening direction. As an alternate, for protecting the cloth of wall 9, the spring 35 can be inserted in a tube 37 of metal or semi-rigid plastic or rubber inserted into channel 21. In the form of force-producing means illustrated in FIG. 6, the spring-means comprises wire 35, and the tube 37 comprises the vertical rigidity means; hence, the rigidity means is separate from the spring-means in this form of the invention.

For all forms of spring-means and rigidity means disclosed herein, and particularly the rubber tube 17, it is very useful to secure at least one of the "legs" of the spring-rigidity element comprising these means to the adjacent cloth so the element remains in place. For example, as seen in FIGS. 4 and 5, one end of tube 17b might be secured to piece 13, as by threads; and the other end of tube 17 might be similarly secured to strip 19. I have found that securing only tube 17 to strip 19 appears to be acceptable. In another form of retaining means, the upper end of sheath 19 can be sewn closed so that, along with seam 14, the tube is trapped (inserted with the pouch inside-out).

FIG. 7 is a line-drawing of a pouch in boxer shorts turned inside out and showing another means to automatically urge the free-wall 9 to move in an opening direction. In this form of pouch-opening means, the cut length A-B-C of the free-wall 9 is longer than the cut-length of the portion A-D-C; this form of opening-means may also be used in the other forms of the invention disclosed herein. The absorbent piece 13 might not be a separate piece, but can be part of the free-wall 9, folded at the bending line 9b. Then the portion A-D-C of piece 13 (sew to the leg-portion 3) is made shorter than the portion A-B-C of wall 9, which tends to urge the wall 9 in an opening direction.

In FIG. 7, still another form of force-producing means is illustrated. In FIG. 7, a spring element 43 which may comprise a flexible rubber tube or chord (with or without a spring-wire inside the tube) is mounted generally horizontally and near the top-portion of the free-wall 9. The gentle force of spring-element 43 tends to urge the free-wall 9 to move in an opening direction. In this form of force-producing means, the rigidity means may comprise a semi-flexible rubber or plastic tube or chord, etc., or a metal strip-member, mounted generally vertically in a sheath 46 (similar to sheath 21).

FIG. 8 shows another form of force-producing means, in which a spring-element 47 is molded (of a form of rubber or plastic) in a particular shape to provide both the spring-action and vertical rigidity for the free-wall 9. The spring element includes flange-portions 47a, a rib-portion 47b to provide sufficient vertical rigidity to the free-wall 9, a spring-portion 47c, preferably with a thinner section, and another rib-portion 47b for attachment to the other inner wall of the pouch. The flange-portion 47a is secured to the free-wall 9, as by seams or by a production adhesive. In a similar manner, the other flange-portion 47a is secured to the absorbent-piece 13, or directly to the leg-portion 3 if absorbent-piece 13 is omitted and if the outside of the leg-portion is treated with a substance similar to "Scotch Gard", but permanently liquid-proof. The molded spring-element 47 can be made of numerous suitable shapes and contours. For example, the spring-portion 47c might have an oval or round section, and the rib-portions might be more rounded and/or tapered, etc. But the main purpose of this element is to provide a molded piece, having a natural spring-rate, which can bend into a generally U-shape and in which the mid-portion 47c provides a proper inherent spring-action (as from a rubber material); and the extremity portions are wider and/or thicker, with ribs to provide the necessary vertical-rigidity. The piece 47 can either be sewn or cemented to the pouch walls, thereby saving the cost of sheath-strip 19 and slot 27. A metal spring-member made of flat spring or wire stock can be molded inside the spring-portion if a more consistent spring-action is needed. Also, a short rigid or weight member 48, such as a ½" to 1" metal rod or strip (1/16"–3/32" dia.) can be molded in the flange-portion 47a, or made to snap into a cavity 47e, as shown, for providing a supplemental weight-action as part of the force-producing means, and also to give slight additional rigidity.

The protector garment made according to the inventive concepts set forth herein is much better in actual use by wearing the garment than it might appear in drawings and by discussion. The reason it works so well is that when the hand with the penis is first inserted through the flap-opening (before and after urination), the hand forces the leg-portion 3 away from the wearer's leg to produce a space. At this time, the wearer's hand with the penis is then inside the undershorts, but has not yet reached the pouch. At the same time, the gentle force of the force-producing means urges the free-wall 9 to "open" automatically away from the leg-portion 3 into this space, so the open chamber 8 is ready and waiting for the hand and penis to enable easy deposit thereof by the wearer. Without the force-producing means, or the form shown in FIG. 7, as mentioned before, the free-wall sometimes tends to cling to the leg-portion as after laundering, which makes it somewhat difficult for the hand and penis to enter chamber 8.

My research has shown that for normal healthy men in Class I and most of Class II, there is no need for a disposable absorbent liner. The normal woven fabric of boxer shorts or the cloth-clad rubberized piece 13 are sufficient to absorb the small amount of liquid (urine or semen) which might be lost from the "residual-liquid column" as defined above, and also because of a slight closure-delay of the sphincter muscle if the garment-wearer is careless. This is true since the garment is changed and washed often. Therefore, the large cost as well as time for insertion and removal of absorbent liners are not necessary for men in Class I and most of Class II, as defined above.

However, for men in the last portion of Class II and the first part of Class III in which the sphincter "valve" has a larger delay in closing, and even starting to remain open, a thin disposable liner having increased absorbency can be used effectively if made according to the present invention, to be inserted and removed from the pouch. Also, a slightly thicker absorbent liner can be used for men in the rest of Class III in which the sphincter muscle never quite closes, so there is a very slow and minute leakage at all times. In FIG. 9, a disposable absorbent insert or liner specifically arranged for the present invention is illustrated. This absorbent liner is intended generally for men who are just beginning to have a real bladder-control problem, and hence reside in Class II and the start of Class III. Men in the rest of Class III and Class IV with a higher degree of bladder-control problem must use other more complete diaper-type bladder-control means, which are now available on the market. Hence, my invention is particularly useful not only for normal healthy men (without using an absorbent liner) but also for almost-normal men who are just beginning to have a bladder-control problem, and hence require a small or thin absorbent liner.

In FIG. 9, an absorbent liner 50 is bent into a U-shape when inserted in the pouch, although it will be sold in its normal flat position, shown in phantom in FIG. 9. The liner has an absorbent portion 52 thicker than the absorbent material bonded to the piece 13 so it can absorb slightly more liquid-drainage. The liner 50 might be about the same thickness as "Panty liners" for women. Another thicker liner can be made available for a slightly higher degree of bladder-control problem for men in Class III. The liner also has a liquid-proof backing sheet 54 (such as plastic or rubberized material) to prevent the liquid from reaching the outer surface of the garment. The backing sheet includes holding means such as adhesive pads 56 and a cover-sheet (not shown) to protect the adhesive strips adhering to the backing sheet; after removing the cover sheet, the wearer presses the adhesive strips against the inside walls of the pouch. When the garment is laundered, the liner must first be removed and discarded.

It is possible to provide a special disposable absorbent liner made according to the present invention. After testing numerous materials for absorbent liners, I found that if the backing sheet is made of the proper material having the correct natural spring-rate but supplied in the flat position (as shown in phantom), the liner itself can provide an acceptable spring-action to urge the free-wall 9 in an opening direction, along with acceptable vertical rigidity for the free-wall 9; this rigidity is provided in the backing sheet 54 by a rib 54a similar to a rib in sheet metal. To facilitate the spring-action, the ends of the liner are shown open; this can be done if the liner is long enough so that the penis resides somewhat near the mid-position of the liner. With this construction, if the plastic or rubber backing sheet is strong enough, the rubber and metal springs 17a and 29 might be reduced, or even possibly omitted along with the sheath 19 and slot 27 when the pouch is intended for use with this special disposable absorbent liner.

The force of the spring-portion 17a is very gentle to move only free-wall 9. If liner 50 has no inherent spring force and is inserted in and attached to pouch 2 (as by adhesive pads 56) the gentle force of spring 17a must also open the liner. Hence, the liner 50 and spring-portion 50a, in this manner becomes part of the total inventive combination disclosed herein.

If the garment is made special for men who are beginning to experience more than normal dribble, then the basic pouch 2 (FIGS. 3,5) may not be needed. In this form of the invention, the pouch might comprise only the absorbent liner 50, similar to FIG. 9; then it must include an inherent spring action and also must include means to attach the pouch (now liner 50) to the leg-portion 3. This form of pouch, if open-ended would require at least a string-like member at the end(s) to limit the opening; or this form might include a cloth support for the "pouch".

The liner 50 can be made of varied shapes, for example by cutting the ends at an angle so the liner in the flat position has a shallow V-shape. If the absorbent-piece 13 is used, the pouch 2 can be formed by making the wall 9 and piece 13 of one piece of cloth folded at the bottom, in order to conform better to the liner 50.

When the sphincter-delay becomes slightly larger than normal, but before insert 50 is needed, the wearer can merely crumple about 3-4 squares of toilet tissue and insert in the bottom of pouch 2 (after urination), and then discard the prior tissues. When the sphincter-delay increases further, then insert 50 can be used.

Now referring to all the concepts disclosed herein, it should be understood that any reversals or modifications of the forms shown do not change the scope of the invention in any way. For example, the main pouch 2 can be made with one or both ends open and folded at the bottom, similar to the liner 50 in FIG. 9; but this pouch-construction might require vertical rigidity-means. However, tests to date indicate that it is preferable to have one or both ends of pouch 2 closed as shown in FIGS. 1-5 and 7. Also, it is possible to provide a garment in which the testicles are held by a snug-fitting portion (as in knit briefs, for example,) while the penis is outside and loose-fitting; however as long as the pouch, per se is made according to the concepts disclosed herein, even this garment would still be within the scope of the present invention. In one possibility, the pouch would be in front of the garment against the pants; however, tests to date indicate that the forms of the invention illustrated herein is preferable, wherein the pouch is inside the garment. Also, the pouch itself might be separate and attachable to be secured to the garment by fastening means, such as by buttons, snaps, "Velcro", etc., as for use in existing boxer shorts or pajamas now in use without a pouch; however, even in this form of the invention, the shape, location and position of the pouch in relation to the rest of the garment is important in accordance with the inventive concept. Heat-sealing means might also be used. Any other such modification or reversal would have no effect in relation to the application of the inventive concepts disclosed herein.

What I claim is:

1. In a protector garment for men adapted to be worn adjacent to the skin of the wearer and including aperture means to form an opening large enough for the penis and the wearer's hand to pass therethrough, the combination comprising: right and left leg-portions of said garment including a large amount of material to provide a substantially predetermined space between the wearer's legs and said leg-portions for producing a generally loose fit on the wearer; a crotch-portion of said garment extending into said leg-portions and including a large amount of material to provide a substantially predetermined space between the wearer and said crotch-portion for enabling the testicles and penis to be suspended substantially free and unrestricted; pouch means including at least a portion thereof operatively connected to one of said leg-portions; said pouch means including means forming an open chamber to receive the penis and including enough material to provide a predetermined large space in said chamber for enabling the penis to remain therein free and unrestricted while said testicles are in said free and unrestricted condition outside said pouch means; said pouch means comprising a size, shape and material mounted in a particular position in relation to said one leg-portion and said aperture means, all to make the wearer feel substantially unaware of the existence of said pouch means; and liquid-absorbent means associated with said pouch means to prevent penis-discharge from reaching the outside surface of said garment.

2. The combination of means defined in claim 1, and said means forming said chamber including a wall thereof having at least a portion movable in relation to said one leg-portion; means to position a top-portion of said movable wall to be generally horizontal for enabling the wearer to have easy access to said open chamber for depositing the penis therein.

3. The combination of means defined in claim 1, and said means forming said chamber including a free wall having at least a portion movable in relation to said one leg-portion; the top-portion of said movable wall having a length sufficiently greater than the corresponding length of said leg-portion at the connected extremities of said wall and said leg-portion, to urge said movable wall in an opening direction.

4. The combination of means defined in claim 1, and said aperture means including inner and outer flap-portions; said one leg-portion including said outer flap portion; said means forming said chamber including a free-wall thereof having at least a portion movable in relation to said one leg-portion; fastening means operatively connecting at least a major portion of said free-wall to said one leg-portion to form said open chamber; said fastening means also acting to position a top-portion of said free-wall to be somewhat near the bottom of said opening of said aperture means and generally horizontal, while the bottom of said movable wall resides a predetermined distance below the bottom of said opening to provide ample space for the penis, all for enabling the wearer to have easy access to said open chamber while being unaware of said pouch means.

5. A protector garment for men adapted to be worn adjacent to the skin of the wearer and including aperture means having inner and outer flap-portions to form an opening large enough for the penis and the wearer's hand to pass therethrough; right and left extended leg-portions of said garment including a large amount of material to provide a substantially predetermined space between the wearer's legs and said leg-portions for producing a generally loose fit on the wearer; a a crotch-portion of said garment extending into said leg-portions and including a large amount of material to provide a substantially predetermined space between the wearer and said crotch-portion for enabling the testicles and penis to be suspended substantially free and unrestricted; pouch means including at least most thereof operatively connected to the inside of only the one of said leg-portions that includes said outer flap-portion; said pouch means including means forming an open chamber to receive the penis and comprising enough material to provide a predetermined large space in said chamber for enabling the penis to remain therein free and unrestricted while said testicles are in said free and unrestricted condition outside said pouch means; said means forming said chamber including a free-wall thereof having at least a portion movable in relation to said one leg-portion; means to position a top-portion of said movable wall somewhat near the bottom of said opening of said aperture means for enabling the wearer to have easy access to said open chamber to deposit the penis therein; said pouch means comprising a size, shape and material mounted in relation to said one leg-portion and said aperture means to make the wearer feel substantially unaware of the existence of said pouch means; and liquid-absorbent means associated with said pouch means to prevent penis-discharge from reaching the outside surface of said garment.

6. A protector garment for men adapted to be worn adjacent to the skin of the wearer and including aperture means to form an opening large enough for the penis and the wearer's hand to pass therethrough; right and left leg-portions of said garment including a large amount of material to provide a substantially predetermined space between the wearer's legs and said leg-portions for producing a generally loose fit on the wearer; a crotch-portion of said garment extending into said leg-portions and including a large amount of material to provide a substantially predetermined space between the wearer and said crotch-portion for enabling the testicles and penis to be suspended substantially free and unrestricted; pouch means for receiving the penis and operatively associated with one of said leg-portions; means to position at least a portion of said pouch means adjacent to said one leg-portion; and pouch means including means forming an open chamber having a space large enough to enable insertion of enough of the wearer's hand with the penis so the same can be deposited easily and remain in said pouch means; and liquid-absorbent means associated with said pouch means to prevent penis-discharge from reaching the outside surface of said garment.

7. The combination of means defined in claim 6, and said aperture means including inner and outer flap-portions; said means forming said chamber including a movable wall operatively associated with the inside of said leg-portion that includes said outer flap-portion; said movable wall having top-portion thereof located by said positioning means to reside somewhat near the bottom of said opening of said aperture means, for enabling the wearer to have easy access to said open chamber for depositing the penis therein.

8. In a protector garment for men adapted to be worn adjacent to the skin of the wearer and including aperture means having inner and outer flap-portions disposed to form an opening large enough for the penis and the wearer's hand to pass therethrough, the combination comprising: right and left extended leg-portions of said garment including a large amount of material to provide a substantially predetermined space between the wearer's legs and said leg-portions for producing a generally loose fit on the wearer; a crotch-portion of said garment extending into said leg-portions and including a large amount of material to provide a substantially predetermined space between the wearer and said crotch-portion for enabling the testicles and penis to be suspended substantially free and unrestricted; pouch means operatively associated with the one of said leg-portions that includes said outer flap-portion; means to position at least a portion of said pouch means adjacent to the inside of said one leg-portion that includes said outer flap-portion; said pouch means including means forming an open chamber large enough for the penis to be deposited therein by the wearer and remain therein free and unrestricted while said testicles are in said free and unrestricted condition outside said pouch means; said pouch means comprising a size, shape and material mounted in a particular position in relation to said one leg-portion and said aperture means, all to make the wearer feel substantially unaware of the existence of said pouch means; and liquid-absorbent means associated with said pouch means to prevent penis-discharge from reaching the outside surface of said garment.

9. The combination of means defined in claim 8, and said means forming said chamber including a wall thereof having at least a portion movable in relation to said one leg-portion; said movable wall having a top-portion thereof located by said positioning means to be generally horizontal and somewhat near the bottom of said opening of said flap-portions for enabling the wearer to have easy access to said open chamber for depositing the penis therein.

10. The combination of means defined in claim 8, and said means forming said chamber including a wall thereof having at least a portion movable in relation to said one leg-portion; said movable wall having a top-portion thereof located by said positioning means to be generally horizontal and somewhat near the bottom of said opening of said flap-portions for enabling the wearer to have easy access to said open chamber; said pouch means including a portion extending a predetermined distance past the mid-position of said leg-portions crotch-portion to the other of said two leg portions to provide ample room for the penis in said chamber.

11. In a protector garment for men adapted to be worn adjacent to the skin of the wearer and including aperture means having inner and outer flap-portions disposed to form an opening for the penis, the combination comprising: right and left leg-portions of said garment large enough to provide a generally loose fit on the wearer; a crotch-portion extending into said leg-portions and also large enough to provide a generally loose fit on the wearer, wherein the testicles and penis are free and unrestricted; pouch means operatively associated with the inside of the one of said leg-portions that includes said outer flap-portion; said pouch means including means forming an open chamber to receive the penis with ample space for enabling the same to remain therein free and unrestricted while said testicles are free and unrestricted outside said pouch means; said means forming said chamber including a free wall thereof movable in relation to said one leg-portion for temporarily rendering said space large enough to enable insertion of enough of the wearer's hand with the penis so the same can be deposited easily and remain in said pouch means; fastening means operatively connecting a portion of said movable wall to said inside of said one leg-portion; said movable wall including a top-portion positioned by said fastening means to be generally horizontal and somewhat near the bottom of said opening of said flap-portions for enabling the wearer to have easy access to said open chamber; and liquid absorbent means associated with said pouch means to prevent penis-discharge from reaching the outside surface of said garment.

12. The combination of means defined in claim 11, and said liquid absorbent means including at least a separate liquid-proof piece adjacent the inside surface of said one leg-portion to form another wall of said chamber; and said liquid-absorbent means including an absorbent material disposed to be adjacent to the inside surface of said piece and exposed to the inside of said chamber.

13. The combination of means defined in claim 11, and said liquid-absorbent means comprising at least a liquid-repellent material applied to said outside surface of said one leg-portion in the vicinity of said pouch means.

14. The combination of means defined in claim 11, and said liquid-absorbent means comprising at least a separate liquid-proof piece adjacent to the inside surface of said one leg-portion to form another wall of said chamber; and said liquid-proof piece including an absorbent material permanently bonded to the inside surface of said piece and exposed to the inside of said chamber.

15. The combination of means defined in claim 11, and said liquid-absorbent means comprising at least a separate liquid-proof piece adjacent to the inside surface of said one leg-portion to form another wall of said chamber; said absorbent means including liquid-absorbent means disposed to be adjacent to the inside surface of said piece and exposed to the inside of said chamber; and said liquid-proof piece having a portion extending below the pouch means a predetermined distance inside said one leg-portion to provide additional protection of said leg-portion from said liquid-discharge.

16. The combination of means defined in claim 11, and said pouch means including a portion extending a predetermined distance past the mid-position of said crotch-portion to the other of said two leg-portions to provide ample room for the penis in said chamber; and said fastening means being adapted to attach at least the upper corner of said extended portion of said pouch means to said other leg-portion.

17. In a garment for men adapted to be worn adjacent to the skin of the wearer and including a crotch-portion and aperture means forming an opening for the penis of said wearer, the combination comprising: pouch means associated with said garment and including a movable wall forming an open chamber to receive the penis; rigidity means associated with said movable wall and including means to provide sufficient vertical rigidity for preventing said movable wall from collapsing during the deposit of the penis into said chamber by the wearer.

18. The combination of means defined in claim 17, and said rigidity means including a relatively rigid member operatively connected to at least a portion of said movable wall in a generally vertical direction; said member tending to be substantially straight in its free position and having at least a portion thereof sufficiently flexible to prevent said member from annoying the wearer.

19. The combination of means defined in claim 8, and said means forming said chamber including a free-wall movable in relation to one of said leg-portions; rigidity means associated with said movable wall to provide sufficient longitudinal rigidity in generally a vertical direction to prevent said wall from collapsing during said deposit of the penis into said chamber by the wearer.

20. In a protector garment for men adapted to be worn adjacent to the skin of the wearer and including aperture means to form an opening for the penis, the combination comprising: right and left leg-portions of said garment large enough to provide a generally loose fit on the wearer; a crotch-portion of said garment extending into said leg-portions and also large enough to provide a generally loose fit on the wearer, wherein the testicles and penis are inherently free and unrestricted; pouch means associated with said garment in substantially one of said leg-portions; said pouch means including means forming an open chamber having a space large enough to enable insertion of enough of the wearer's hand with the penis so the same can be deposited easily and remain in said pouch means; said means forming said chamber including a movable free wall; rigidity means associated with said movable wall to provide sufficient longitudinal rigidity in generally a vertical direction for preventing said movable wall from collapsing during the deposit of the penis into said chamber by the wearer; and liquid-absorbent means associated with said pouch means to prevent penis-discharge from reaching the outside surface of said garment.

21. The combination of means defined in claim 20, and said rigidity means comprising a rubber-like strip-member operatively connected to said movable wall in said generally vertical direction.

22. A garment for men adapted to be worn adjacent to the skin of the wearer and including a crotch-portion; pouch means associated with said garment near said crotch-portion and having an openable chamber to receive the penis of said wearer; said pouch means including means to automatically increase the opening of said chamber temporarily to enable easy deposit of the penis into said chamber by the wearer.

23. A garment for men adapted to be worn adjacent to the skin of the wearer and including a crotch-portion; pouch means associated with said garment near said crotch-portion and including means forming an openable chamber to receive the penis of said wearer; and force-producing means operatively associated with said means forming said chamber for producing a gentle force acting thereon to automatically increase the opening of said chamber temporarily to enable easy deposit of the penis into said chamber by the wearer.

24. In a garment for men adapted to be worn adjacent to the skin of the wearer and including a crotch-portion and aperture means forming an opening for the penis of the wearer, the combination comprising: pouch means operatively associated with said garment near said aperture means and including a movable free-wall forming an open chamber to receive the penis; said pouch means including opening means operatively associated with said free-wall and acting thereon to move same automatically in an opening direction for enabling easy deposit of the penis into said open chamber by the wearer.

25. In a garment for men adapted to be worn adjacent to the skin of the wearer and including a crotch-portion and aperture means forming an opening for the penis of said wearer, the combination comprising: pouch means associated with said garment near said aperture means and including a movable free wall forming an open chamber to receive the penis; and force-producing means operatively associated with said pouch means for producing a gentle force acting on said movable wall to move same automatically in an opening direction for enabling easy deposit of the penis into said open chamber by the wearer.

26. In a garment for men adapted to be worn adjacent to the skin of the wearer and including a crotch-portion and two leg-portions, and also including aperture means forming an opening for the penis of said wearer, the combination comprising: pouch means associated with said garment near said aperture means and including means forming an open chamber having large enough space to enable insertion of enough of the wearer's hand with the penis so same can be deposited easily in said chamber and remain therein; said means forming said chamber including a free wall movable in relation to one of said leg-portions; and spring-means operatively connected to said movable wall and to said one leg-portion for causing said wall to move away from said one leg-portion with a sufficiently light force to prevent unobtrusive bulging of said one leg-portion in normal wear of said garment while providing said large open space for said chamber.

27. The combination of means defined in claim 26, and said spring means comprising a rubber-like element having a central portion providing a spring-rate when said element is bent in a generally U-shape; said element including a generally vertical extended portion thereof operatively connected to said movable wall; rigidity means associated with said movable wall and having sufficient rigidity to prevent collapse thereof when the penis is deposited into said chamber by the wearer; said element including a second extended portion operatively connected to said one leg-portion, to produce said light force acting on said free wall.

28. In a protector garment for men adapted to be worn adjacent to the skin of the wearer and including aperture means to form an opening for the penis, the combination comprising: right and left leg-portions of said garment large enough to provide a generally loose fit on the wearer; a crotch-portion of said garment extending into said leg-portions and also large enough to provide a generally loose fit on the wearer, wherein the testicles and penis are inherently free and unrestricted; pouch means associated with one of said leg-portions; said pouch means including means forming an open chamber to receive the penis with ample space for enabling the penis to be deposited easily therein and remain free and unrestricted while said testicles are free and unrestricted outside said pouch means; said means forming said chamber including a free-wall movable in relation to one of said leg-portions; said pouch means including opening means operatively associated with said free-wall and acting thereon to move same automatically in an opening direction for enabling said easy deposit of the penis into said open chamber by the wearer; and liquid-absorbent means associated with said pouch means to prevent penis-discharge from reaching the outside surface of said garment.

29. In a protector garment for men adapted to be worn adjacent to the skin of the wearer and including aperture means to form an opening for the penis, the combination comprising: right and left leg-portions of said garment large enough to provide a generally loose fit on the wearer; a crotch-portion of said garment extending into said leg-portions and also large enough to provide a generally loose fit on the wearer, wherein the testicles and penis are inherently free and unrestricted; pouch means operatively associated with at least one of said leg-portions; said pouch means including means forming an open chamber having a space large enough to enable insertion of enough of the wearer's hand with the penis so the same can be deposited easily and remain in said pouch means, said means forming said chamber including a free wall movable in relation to one of said leg-portions; force-producing means operatively associated with said pouch means and acting on said movable wall with a gentle force to move same automatically in an opening direction away from said one leg-portion for enabling said easy deposit of the penis into said open chamber by the wearer; and liquid-absorbent means associated with said pouch means to prevent penis-discharge from reaching the outside surface of said garment.

30. The combination of means defined in claim 29, and said force-producing means comprising a combination of spring means and weight means; and means for operatively connecting said last two means to said movable wall to cause said movement thereof in said opening direction.

31. The combination of means defined in claim 29, and said force-producing means comprising a strip-like element having a central portion acting as a spring; said movable wall including vertical sheath means; said pouch means having a second wall including another vertical sheath means; said element having one extended portion inserted into one of said sheath means and having a second extended portion inserted into the other of said sheath means, to provide said gentle spring force acting on said movable wall.

32. The combination of means defined in claim 29, and said liquid-absorbent means comprising a disposable liner having a relatively movable portion and including absorbent material and adapted to be inserted in said chamber and removable therefrom; said force-producing means comprising at least a liquid-proof backing member bonded to said absorbent material and having a central portion producing a spring-rate in bending to provide said gentle force acting on said movable liner-portion and said movable wall; and holding means associated with said backing member to retain said liner inside said chamber until removed by the garment wearer.

33. The combination of means defined in claim 29, and said liquid-absorbent means comprising a disposable liner having a relatively movable portion and including absorbent material and adapted to be inserted in said chamber and removable therefrom; said force-producing means comprising at least a liquid-proof backing member bonded to said absorbent material and having a central portion producing a spring-rate in bending to provide said gentle force acting on said movable liner-portion and said movable wall; holding means associated with said backing member to retain said liner inside said chamber until removed by the garment-wearer, said backing member including a generally vertical portion extending from said central portion and positioned adjacent said movable wall; said vertical portion including means independent of said central portion to provide sufficient rigidity for preventing the collapse of said movable wall when the penis is deposited in said chamber.

34. In a garment for men adapted to be worn adjacent to the skin of the wearer and including a crotch-portion and aperture means forming an opening for the penis of the wearer, the combination comprising: pouch means associated with said garment near said aperture means and including a movable free wall forming an open chamber to receive the penis; force-producing means operatively associated with said pouch means and acting on said movable wall with a gentle force to move same automatically in an opening direction for enabling easy deposit of the penis into said open chamber by the wearer; and said force-producing means comprising at least weight means operatively connected to said wall for causing same to move in said opening direction away from said one leg-portion.

35. In a protector garment for men adapted to be worn adjacent to the skin of the wearer and including aperture means having inner and outer flap-portions disposed to form an opening for the penis, the combination comprising: right and left leg-portions of said garment large enough to provide a generally loose fit on the wearer; a crotch-portion extending into said leg-portions and also large enough to provide a generally loose fit on the wearer, wherein the testicles and penis are free and unrestricted; pouch means operatively associated with the inside of the one of said leg-portions that includes said outer flap-portion; said pouch means including means forming an open chamber to receive the penis with ample space for enabling the same to remain therein free and unrestricted while said testicles are free and unrestricted outside said pouch means; said means forming said chamber including a free wall thereof movable in relation to said one leg-portion for temporarily rendering said space large enough to enable insertion of enough of the wearer's hand with the penis so the same can be deposited easily and remain in said pouch means; fastening means operatively connecting a portion of said movable wall to said inside of said one leg-portion; said movable wall including a top-portion positioned by said fastening means to be generally horizontal and somewhat near the bottom of said opening of said flap-portions for enabling the wearer to have easy access to said open chamber; force-producing means operatively associated with said pouch means and acting on said movable wall with a gentle force to move same automatically in an opening direction away from said one leg-portion for enabling said easy deposit of the penis in said pouch means after same is open; and liquid-absorbent means associated with said pouch means to prevent penis-discharge from reaching the outside surface of said garment.

36. In a protector garment for men adapted to be worn adjacent to the skin of the wearer and including aperture means to form an opening large enough for the penis and the wearer's hand to pass therethrough; the combination comprising: right and left leg-portions of said garment including a large amount of material to provide a substantially predetermined space between the wearer's legs and said leg-portions for producing a generally loose fit on the wearer; a crotch-portion of said garment extending into said leg-portions and including a large amount of material to provide a substantially predetermined space between the wearer and said crotch-portion for enabling the testicles and penis to be suspended substantially free and unrestricted; pouch means for receiving the penis and operatively connected to one of said leg-portions; said pouch means including means forming an open chamber having a space large enough to enable insertion of enough of the wearer's hand with the penis so the same can be deposited easily and remain in said pouch means; means operatively connecting at least most of said pouch means to only said one leg-portion; said pouch means including a portion extending a predetermined distance past the mid-position of said crotch-portion to the other of said two leg-portions to provide ample room for the penis in said chamber; and liquid-absorbent means associated with said pouch means to prevent penis discharge from reaching the outside surface of said garment.

37. In a protector garment for men adapted to be worn adjacent to the skin of the wearer and including aperture means having inner and outer flap-portions disposed to form an opening large enough for the penis and the wearer's hand to pass therethrough, the combination comprising: right and left extended leg-portions of said garment including a large amount of material to provide a substantially predetermined space between the wearer's legs and said leg-portions for producing a generally loose fit on the wearer; a crotch-portion of said garment extending into said leg-portions and including a large amount of material to provide a substantially predetermined space between the wearer and said crotch-portion for enabling the testicles and penis to be suspended substantially free and unrestricted; pouch means including at least a main portion thereof operatively connected to the inside of said one leg-portion that includes said outer flap-portion; said pouch means including means forming an open chamber large enough for the penis to be deposited therein by the wearer and remain therein free and unrestricted while said testicles are in said free and unrestricted condition outside said pouch means; and liquid-absorbent means associated with said pouch means to prevent penis-discharge from reaching the outside surface of said garment; said liquid-absorbent means comprising at least a separate replaceable liner including liquid-absorbent material and adapted to be inserted into said large open chamber to form a generally U-shape in bending and readily removable from said chamber; said pouch means comprising a size, shape and material mounted in a particular position in relation to said one leg-portion and said aperture means, all to make the wearer feel substantially unaware of the existence of said pouch means and said liner.

38. In a protector garment for men adapted to be worn adjacent to the skin of the wearer and including aperture means to form an opening large enough for the penis and the wearer's hand to pass therethrough, the combination comprising: right and left extended leg-portions of said garment including a large amount of material to provide a substantially predetermined space between the wearer's legs and said leg-portions for producing a generally loose fit on the wearer; said aperture means including inner flap-portions extending into a first of said two leg-portions and an outer flap-portion extending into the second of said two leg portions; a crotch-portion of said garment extending into said leg-portions and including a large amount of material to provide a substantially predetermined space between the wearer and said crotch-portion for enabling the testicles and penis to be suspended substantially free and unrestricted; pouch means for receiving the penis and operatively associated with said second-named leg-portion; said pouch means including means forming an open chamber and comprising sufficient material to provide a predetermined large space in said chamber for enabling insertion of enough of the wearer's hand with the penis so the same can be deposited easily therein; said means forming said chamber comprising a free-wall including at least a top-portion thereof freely movable in relation to said second-named leg-portion to facilitate said large open chamber; means to position at least a majority segment of said pouch means adjacent to only said second-named leg-portion on the inside thereof for enabling the penis to be deposited directly into said open chamber; said positioning means also being disposed to locate said top-portion of said free-wall to be somewhat near the bottom of said opening of said aperture means and generally horizontal, and to provide a predetermined depth of said pouch means for enabling said large space; and liquid-absorbent means associated with said pouch means at least adjacent to said second-named leg-portion to prevent penis-discharge from reaching the outside surface of said garment; the said combination of means being disposed and arranged to make the wearer feel substantially unaware of the existence of said pouch means.

39. The combination of means defined in claim 38, and said pouch means including a minor segment thereof extending a predetermined distance past the mid-position of said crotch-portion to said first-named leg-portion for facilitating said large space in said chamber and said unawareness of said pouch means.

40. The combination of means defined in claim 38, and said pouch means including a minor segment thereof extending a predetermined distance past the mid-position of said crotch-portion to said first-named leg-portion for facilitating said large space in said chamber and said unawareness of said pouch means; force-producing means operatively associated with said free-wall for producing a gentle force acting thereon to move same automatically in an opening direction away from said second-named leg-portion; rigidity means associated with said free-wall and co-acting with said force-producing means to provide sufficient longitudinal rigidity of said wall in a generally vertical direction for preventing said free-wall from collapsing during said deposit of the penis into said chamber while said force-producing means moves said free-wall in said opening direction.

41. The combination of means defined in claim 38, and force-producing means operatively associated with said free-wall for producing a gentle force acting thereon to move same automatically in an opening direction away from said second-named leg-portion; said force-producing means comprising a longitudinal spring element including a first segment operatively connected to said free-wall and a second segment operatively connected to said second-named leg-portion; said element also including a U-shaped portion acting as a spring to produce said gentle force causing said first segment to urge said free-wall in said opening direction.

42. The combination of means defined in claim 38, and rigidity means operatively associated with said free-wall to provide sufficient longitudinal rigidity thereof in a generally vertical direction for preventing said free-wall from collapsing during the deposit of the penis into said chamber by the wearer; said rigidity means comprising a longitudinal element operatively connected to said free-wall in said vertical direction to provide said longitudinal rigidity of said wall; and said longitudinal element having at least a portion thereof sufficiently flexible to prevent said rigidity means from producing discomfort for the wearer.

43. The combination of means defined in caim 29, and said force-producing means comprising at least weight means; and means for operatively connecting said weight means to said movable wall to effect said movement thereof in said opening direction.

44. The combination of means defined in claim 38, and force-producing means associated with said pouch means and acting on said free-wall with a gentle force to move same automatically in an opening direction away from said second-named leg-portion; said force-producing means comprising at least weight means operatively connected to said free-wall and acting thereon to urge same in said opening direction.

45. The combination of means defined in claim 38, and force-producing means operatively associated with said free-wall for producing a gentle force acting thereon to move same automatically in an opening direction away from said second-named leg-portion; rigidity means associated with said free-wall and co-acting with said force-producing means to provide sufficient longitudinal rigidity of said wall in a generally vertical direction for preventing said free-wall from collapsing during said deposit of the penis into said chamber while said force-producing means moves said free-wall in said opening direction; said rigidity means comprising a longitudinal member including a somewhat flexible portion operatively connected to said free-wall in a substantially vertical direction to provide said longitudinal rigidity of said wall; said force-producing means comprising at least a longitudinal spring portion having a generally U-shape for said co-action with said longitudinal member to urge said free-wall in said opening direction.

46. The combination of means defined in claim 28, and said pouch means including a portion extending a predetermined distance past the mid-position of said crotch-portion to the other of said two leg-portions to provide ample room for the penis in said open chamber.

* * * * *